(12) United States Patent
Collazo (10) Patent No.: US 8,047,652 B1
(45) Date of Patent: Nov. 1, 2011

(54) PORTABLE ELECTRONIC AMSLER TEST

(76) Inventor: Ernesto Collazo, Guaynabo, PR (US)

( * ) Notice: Subject to any disclaimer, the term of this patent is extended or adjusted under 35 U.S.C. 154(b) by 0 days.

(21) Appl. No.: 12/708,206

(22) Filed: Feb. 18, 2010

Related U.S. Application Data (60) Provisional application No. 61/179,560, filed on May 19, 2009.

(51) Int. Cl.
*A61B 3/02* (2006.01)

(52) U.S. Cl. .......... 351/223; 351/239; 351/244

(58) Field of Classification Search .......... 351/222, 351/223, 224, 239, 243, 244
See application file for complete search history.

(56) References Cited

U.S. PATENT DOCUMENTS

| | | |
|---|---|---|
| 5,589,897 A | 12/1996 | Sinclair et al. |
| 5,646,710 A | 7/1997 | Caskey |
| 5,737,060 A | 4/1998 | Kasha, Jr. |
| 5,838,422 A | 11/1998 | Caskey |
| 5,892,570 A | 4/1999 | Stevens |
| 6,293,675 B1 | 9/2001 | Eger |
| 6,578,966 B2 | 6/2003 | Fink et al. |
| 6,585,376 B1 | 7/2003 | Matsumoto |
| 6,656,131 B2 | 12/2003 | Alster et al. |
| 6,742,894 B2 | 6/2004 | Stewart |
| 7,220,000 B2 | 5/2007 | Alster et al. |
| 7,275,830 B2 | 10/2007 | Alster et al. |
| 2008/0309879 A1* | 12/2008 | Hirji .................. 351/223 |

* cited by examiner

*Primary Examiner* — Huy K Mai (74) *Attorney, Agent, or Firm* — Luis Figarella (57) ABSTRACT

A method, system and apparatus are provided for portable evaluation of metamophopsia. The method, system and apparatus includes a computer application capable of making any handset or portable display terminal into a portable electronic eye evaluation unit, including clinician's and/or automated assistance, test evaluation and re-test if required.

12 Claims, 7 Drawing Sheets

PORTABLE ELECTRONIC AMSLER TEST

CROSS-REFERENCE TO RELATED APPLICATIONS

The present application claims priority under 35 §U.S.C. 119 to U.S. Provisional patent application No. 61/179,560, entitled "Portable Self-administered Electronic Amsler Test" filed on May 19th, 2009, which is incorporated by reference in its entirety.

FIELD

This application pertains to the field of self-administered visual diagnostic tests, and more particular to field of administration, diagnosis and data management of a hand-held and portable electronic Amsler test in a self-administered electronic format, where the user data input during the test is captured and saved either locally and/or remotely as well as potentially transmitted in either a real time or batch mode.

BACKGROUND

Disorders of the central retina (known as the macula) such as age-related macular degeneration (ARMD) and diabetic retinopathy are the leading cause of severe visual loss among older adults in the Western world. In their early stages these diseases might cause mild changes in the macula with minimal loss of vision. In some patients the disease can advance to a more visually debilitating stage characterized by the development of abnormal new vessels in the macula, a process known as neovascularization. If left untreated, these abnormal vessels leak plasma leading to edema of the macula and later can bleed causing permanent loss of central vision. If some of these pathological changes are detected in early stages, laser photocoagulation of neovascular nets can slow or prevent the development of advanced disease.

One of the early symptoms of disease progression is distortion of central vision known as Metamorphopsia. Metamorphopsia is a geometric distortion of the central visual field. A patient with metamorphopsia often complains that edges that should be straight (such as the edge of a door or window) instead appear bent in the affected regions of the visual field. As this is an early symptom of disease progression, being able to detect it as early as possible can be critical in the early diagnosis and treatment of these sight threatening conditions.

A common clinical approach for detecting and documenting metamorphopsia is to use an Amsler grid, which is a printed square grid, usually 10 cm wide and 10 cm high, containing equally spaced, parallel horizontal and vertical lines. Typical embodiments of the printed grid include individual 5 mm×5 mm squares of equal area, arranged around a fixation point (such as a dot) at the center of the grid. In use, the grid is held at arm's length, e.g. a distance of about 28-30 cm, while one eye is occluded, and the open eye fixes on the central fixation point. Areas of distortion or wavy lines are then noted by the subject, who may draw a circle around the areas of grid distortion. The subject is usually given a smaller, credit card sized, version of the Amsler grid (known as a pocket Amsler card) so that he or she may self-perform the test at home at regular intervals or whenever he or she suspects changes in vision. The subjects are instructed to immediately report any changes in the severity or distribution of the distortion, as these may indicate progression of the disease that requires immediate treatment.

A need exists in the art for an easy to use, hand-held, portable electronic version of the Amsler test (in all applicable sizes, including the full, pocket-card and any intermediate sizes) that would allow people suffering from diseases that affect the macula to be reminded automatically or remotely of the need to perform the Amsler test, in a simple and cost-conscious way, at a time and place of their choosing, with the ability to record and transmit the results in electronic format, perhaps even tailor the test to their already known clinical condition.

This information could then be sent electronically to a printer, storage and/or another electronic device, making the results available to doctors, physicians, nurses, technicians or other health providers (collectively called clinicians here) to review, asses and determine corrective treatment actions. In addition, the results could be made automatically part of the patients Electronic Medical Records (EMR), or electronically processed to display not only test results, but also test statistics to clinicians.

SUMMARY

This section is for the purpose of summarizing some aspects of the present invention and to briefly introduce some preferred embodiments. Simplifications or omissions may be made to avoid obscuring the purpose of the section. Such simplifications or omissions are not intended to limit the scope of the present invention.

In one aspect, the invention would implement the Amsler grid electronically in a hand-held portable electronic device, such as a Handset, Tablet PC, Portable Data terminal, cell phone, Smartphone, electronic book, portable music player or any other such portable computer with graphical capabilities, processor, memory and an input device.

Such an input device could comprise a finger, stylus, touch screen, keyboard, mouse, trackball, trackpad, mousepad, keyboard or other input device. The patient, test subject or user would be able see an electronic representation of an Amsler chart at the correct feature size, and they would be able to record the area of distortion by interfacing with the screen of the device containing the graphical representation of the Amsler grid using a finger, stylus or other appropriate input device. The user input for each test would then be recorded by the device (including ID, time and date and other appropriate tags) so they can be electronically transmitted or shown to the clinician at a latter date. The ability to save multiple images will aid in evaluating disease progression.

In another aspect, the implementation of such a test in such a portable electronic device would be enhanced by the ability of such a device to be either continually or partially connected via a wireless network, such as the cell phone network, WiFi connection, 3G network connection or similar means to the Internet.

In another aspect, the ability of having the test hosted by a computing device would allow users to be reminded in a regular or programmable fashion of the need to perform the test. Similarly, when the portable computing device is linked to a network (be it telephonically, via cables or wirelessly), then tests could be commanded remotely by 3rd parties (including the clinician's office), could be enhanced to include live instructions from an attendant, computer program or clinician. In another aspect, a quick remote evaluation by a qualified clinician or computer program, would include a request for a re-test if the evaluation found this necessary.

In another aspect, the device would interface so as to include test results and other data as part of an Electronic Medical Record (EMR) system where the test is performed by either a user alone or with clinician assistance, and the test results are recorded and saved in the patient's electronic medical record for later review.

Other objects, features and advantages of the present invention will become apparent upon examining the following detailed description of an embodiment thereof, taken in conjunction with the attached drawings. The present invention may be implements in many forms including a system, device, method, or parts thereof.

BRIEF DESCRIPTION OF THE DRAWINGS

The foregoing discussion will be understood more readily from the following detailed description of the invention with reference to the following drawings

DESCRIPTION OF CERTAIN ILLUSTRATIVE EMBODIMENTS

To provide an overall understanding of the invention, certain illustrative embodiments will now be described, including apparatus and methods for displaying images. However, it will be understood by one of ordinary skill in the art that the systems and methods described herein may be adapted and modified as is appropriate for the application being addressed and that the systems and methods described herein may be employed in other suitable applications, and that such other additions and modifications will not depart from the scope hereof.

Figure 1A:
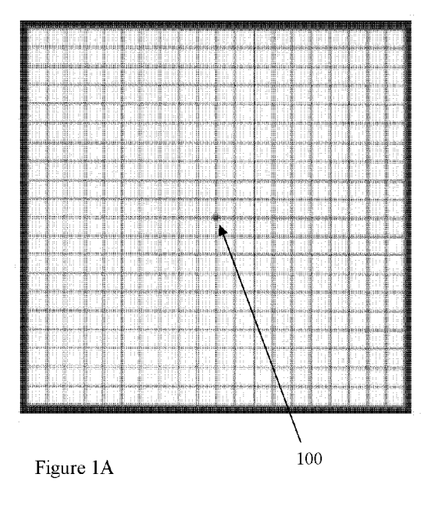
FIG. 1A illustrates what an Amsler chart looks like to a person with normal vision.
Figure 1B:
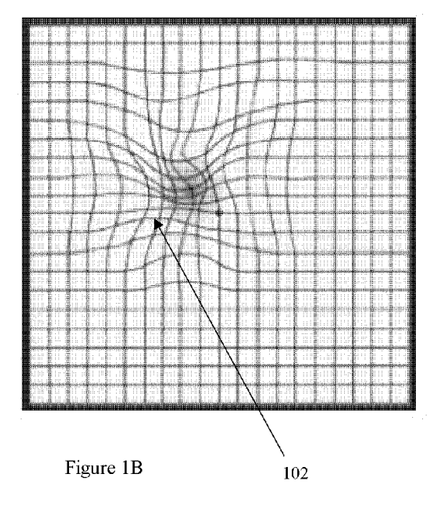
FIG. 1B illustrates what an Amsler chart looks like to a person suffering macular degeneration.

An Amsler chart is a common test for metamorphopsis. To illustrate the effects of macular degeneration on the eye, FIG. 1A illustrates what an Amsler chart looks like to a person with normal vision. There is a central point for optical fixation 100, and no areas where the lines are missing or distorted. In a person with macular degeneration and other macular diseases, the lines at or near the center become distorted or impossible to see. FIG. 1B illustrates what this type of distortion (the area around 102) would look like to a person suffering macular degeneration. As the disease progresses, the distortions can get worse, until central vision is severely degraded and even completely lost.

Figure 2:
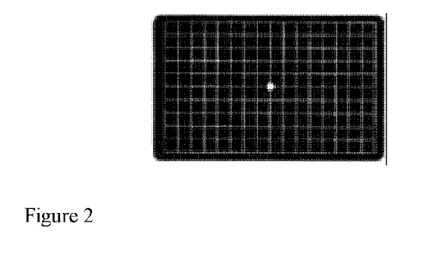
FIG. 2 illustrates the Amsler card that a patient presently is given to take home.

In order to detect and tract the effects of these conditions, patients are given a paper or plastic Amsler chart, and asked to regularly perform a self-test, where they plot the area of the chart they are having trouble with. FIG. 2 illustrates the Amsler card that a patient presently is given to take home. It is typically the same size as a credit card (85.60×53.98 mm), having 5 mm×5 mm squares.

In one embodiment of the invention, a version of the Amsler chart is created electronically in the display of a portable electronic device, which may be a handheld unit. In alternate embodiments, Amsler charts of a size limited by the display device are created. The group of devices comprising such a unit include; devices such as a cellular telephone, Smartphones, electronic portable platforms such as the iPhone or Blackberry, or any other type of portable computers or data pads capable of displaying and capturing user input.

Figure 3:
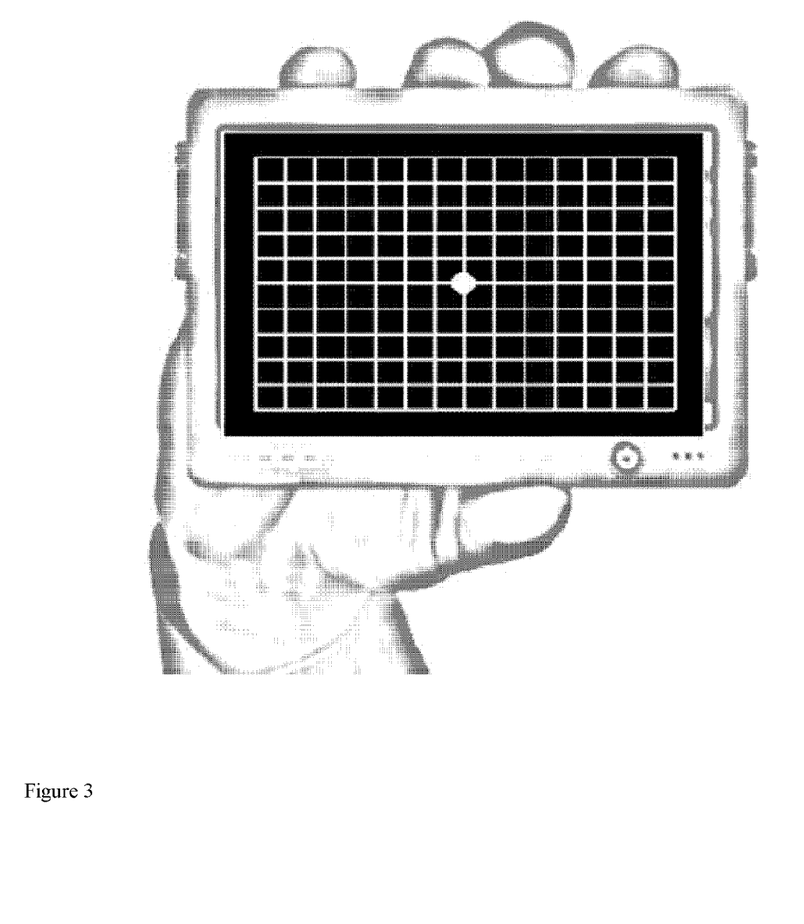
FIG. 3 illustrates the Amsler chart implemented on an iPhone.

Some of the important characteristics for this electronic representation are the central fixation spot and the equally sized squares (usually, but not necessarily, 5 mm×5 mm) regardless of the total size of the Amsler grid within the display. In this fashion, the total size of the Amsler grid presented to the user may vary from one electronic device to another without affecting the usefulness of the test. The color of the lines can also vary as long as there is a high contrast between the lines and the background (e.g. white lines on a black background, red lines on a black background, black lines on a white background, etc.) FIG. 3 illustrates an exemplary illustrative implementation of the electronic Amsler chart on an iPhone handset device.

In one embodiment, the Amsler grid is graphically generated within said portable electronic device or portable handset, data terminal, cell phone or any other such portable computer platform by its processors or graphic driver native graphical capabilities. The processor contains the ability to generate the Amsler chart, using correct display physical qualities, to ensure the Amsler grids are the correct physical size.

In an alternate embodiment, the portable electronic device does not generate the Amsler chart, but proceeds to display a file that contains a graphical representation of the Amsler grid, and is calibrated to the display's device (so as to have the correct 5 mm squares given the known display dimensions of the specific display device).

In another embodiment, the device does not have the Amsler grid file in the local device memory, but instead displays the chart within the device's Internet browser window. The device browser is linked via a network to another computer containing the file to display, which may or may not be specifically targeted to the display of the handset. In effect, the electronic Amsler chart represented in the device is actually a web-page in the server across the network. In this embodiment, care is taken to ensure the actual physical representation of the chart in the device is correct in the dimensions.

Figure 1C:
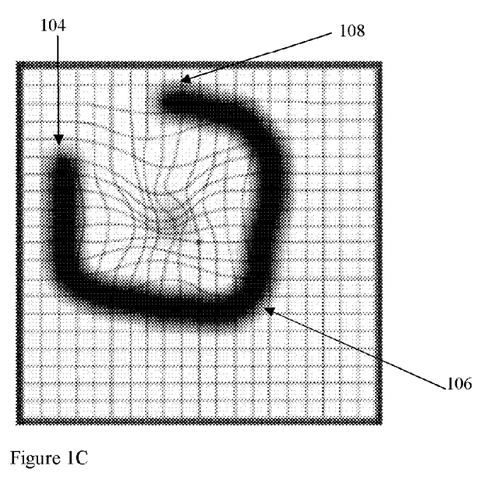
FIG. 1C illustrates an exemplary user's test selection of the areas of concern.

During the test, the device display shows this Amsler chart to the user, and takes their input during the self-evaluation as described before, be it via a pointing device (or finger), or by moving a cursor within the display via the cursor control mechanisms. The user is shown (FIG. 1C) the correct Amsler chart within the device's display, and proceeds to use a data input device to describe the portions 104, 106, 108 of the chart that he/she sees as distorted.

Figure 1D:
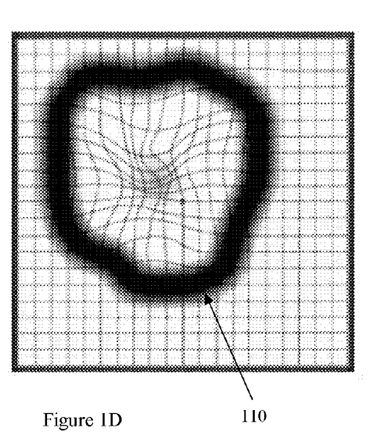
FIG. 1D illustrates an exemplary user's Amsler test result.

While not a requirement, in many cases the clinician will ask the user to complete the periphery of the distorted area (FIG. 1D). In one embodiment, this data input is done by pressing with a finger, mechanical stylus, magnetic stylus, optical stylus, light pen or such other pointing implement interfacing with the devices touch or input screen. One of the advantages of using a stylus over a finger would be the ability to perform the traces with significant increase in accuracy and minimal resolution, resulting from the finer mechanical pointing accuracy of the tip of a stylus or pen, over that of a human finger.

In an alternate embodiment, the user is encouraged to completely cover with their finger, stylus of mouse the complete area of interest perceived by the eye being tested.

In one embodiment, cursor movement using the display's cursor control mechanism (such as the device's trackball, mouse, trackpad, keyboard or any other such cursor control mechanism) for the device's screen is used.

For all input mechanisms used, one embodiment would use electronic filtering of the input signal (such as a low pass filter or covariance filter) to minimize any shaking or jittery motion on the part of the user as they move the cursor over the Amsler Grid.

The actual area 110 selected by the user as having distortions is stored as a graphical overlay in one embodiment. In another, as a series of mathematical vectors. In one embodiment, the areas is stored as a series of X-Y coordinates, whose connection will replicate the user's selection. Any of these is collectively known as the user's test result. In some cases, the result may be communicated as a actual captured/distorted image (see FIG. 1D), while in another embodiment the portable electronic device will download the Cartesian or other geometric coordinates indicating the portion of the screen the patient identified as problematic, it's vector components or any related mathematical representation of the patient input.

To assist some users with the calculation of correct distance for the test, one embodiment would assist them by providing an external distance measuring device to the patient in order to assist them in getting the right distance from their eye or face when performing the test. This may comprise a stick, cane, ruler, tape measure, or other known distance assistance device of a fixed, telescopic or folding assembly nature. Such devices may be tailored for the particular display size in the patient's handset.

Figure 4:
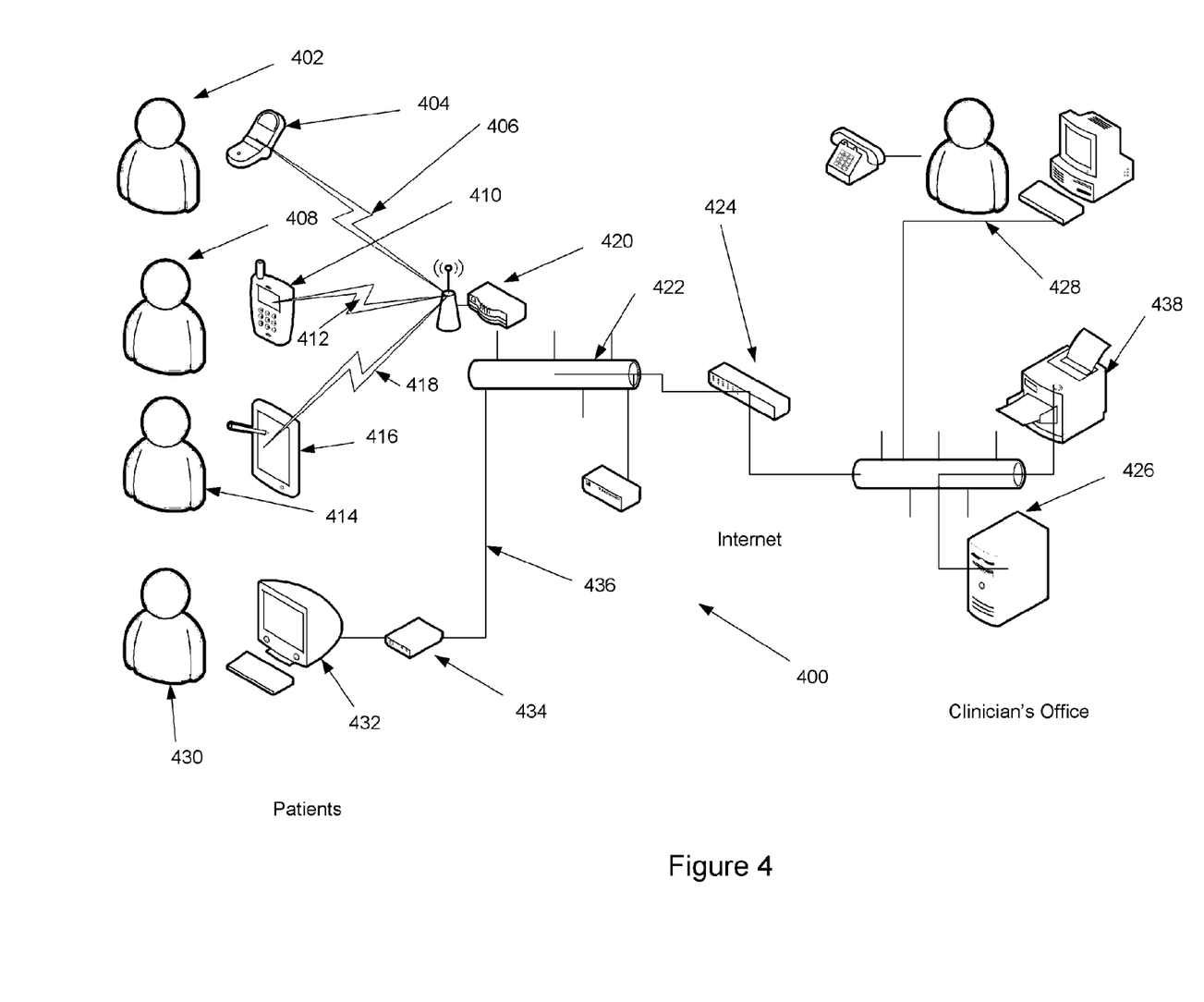
FIG. 4 is a system diagram of various exemplary users interacting within the system and the clinician's office, according to an illustrative embodiment of the invention.

FIG. 4 illustrates various exemplary embodiments of possible user test interactions with the system 400. In on embodiment, a user 402 performs the self evaluation using a cell phone 404, which is connected via a wireless link 406 to a cellular base station 420 which acts as a gateway to the network. The wireless links interface through a base station 420 which is linked through a backbone 422 (may be an internet-type link or Virtual Private network) via a bridge 424 to the computer server 426 used by the Clinician's office 428 (which itself may or may not be located at the location of the clinician).

In another embodiment, the user 408 performs the test using a Smartphone 410 also connected via a wireless link 412. In an alternate embodiment, the user 414 uses a stylus or finger to take the test on an portable graphic interface driven telephone or tablet 416 (these may comprise Smartphone devices like the iPhone or Blackberry, or Tablets such as the Nokia N810, PC Tablets or such other interactive portable computer platforms). In alternate embodiments, these may or may not be linked via a wireless or wired link 418.

Figure 5:
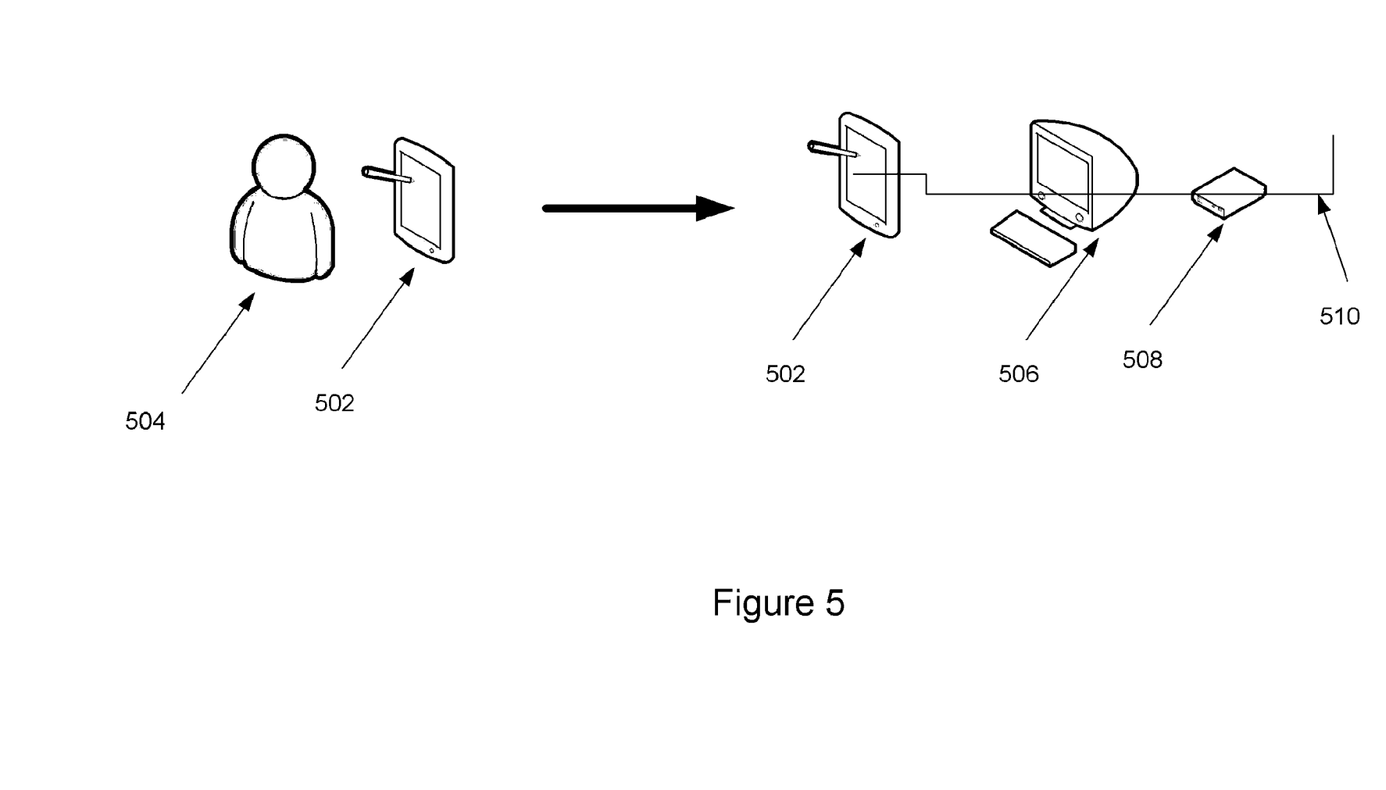
FIG. 5 illustrates an exemplary user using the system in portable, non-networked mode and later uploading test results according to an illustrative embodiment of the invention.

In one embodiment (FIG. 5) the test delivery platform 502 may be devoid of a wireless interface (as is the case of some Apple iTouch), and the patient 504 (or patients, for the test device may be shared) each take one or more tests whose results are locally stored in one or more test files. At some point, the test delivery platform (or its memory module, as may be the case where the embodiment utilizes removable memory modules) is linked (via a cradle, memory chip, Personal Area Network (such as Bluetooth)) or physical cable connection) to a computer 506 connected via Modem 508 to an external network 510 (such as the Internet), and the results of one or more tests for one or more test subjects is uploaded to a clinician.

In another embodiment, the patient 430 may elect to have the test receive the test at computer or terminal 430 connected to the Clinician's office via a wired or wireless network 436 via a device such as a cable modem 434 (or other wired Wide Area Network devices such as DSL, FIOS, Fiber optic or others). In one embodiment, the test results are printed in the clinician's printer 438.

Once the user interacts with the portable electronic Amsler test chart, the device proceeds to capture and store both the results of the test, as well as ancillary user information. In one embodiment, this may comprise information such as Device phone number, device identification, User ID, Patient Name, Unique Identification (Social Security, Patient Number, e-mail address, clinician assigned ID), image of the face of the tester, test information (e.g. date, time of test, total time elapsed during the test), whether the test was initiated by the patient or by the central system, and any other useful test conditions. The data (collectively known as the test results or test records) could be logged and protected against accidental disclosure (via optional encryption) so that it may be securely electronically transmitted (via any of the links discussed herein) or shown to the doctor (on the device itself) at a latter date.

In cases where a connection or link is available to the test device, the real-time, or near real-time uploading of the test results to a server for storage and analysis, and even interaction with a clinician's office (via SMS, 3G, WiFi, WiMax or any other suitable connection between the test device and a server) may take place.

Figure 6:
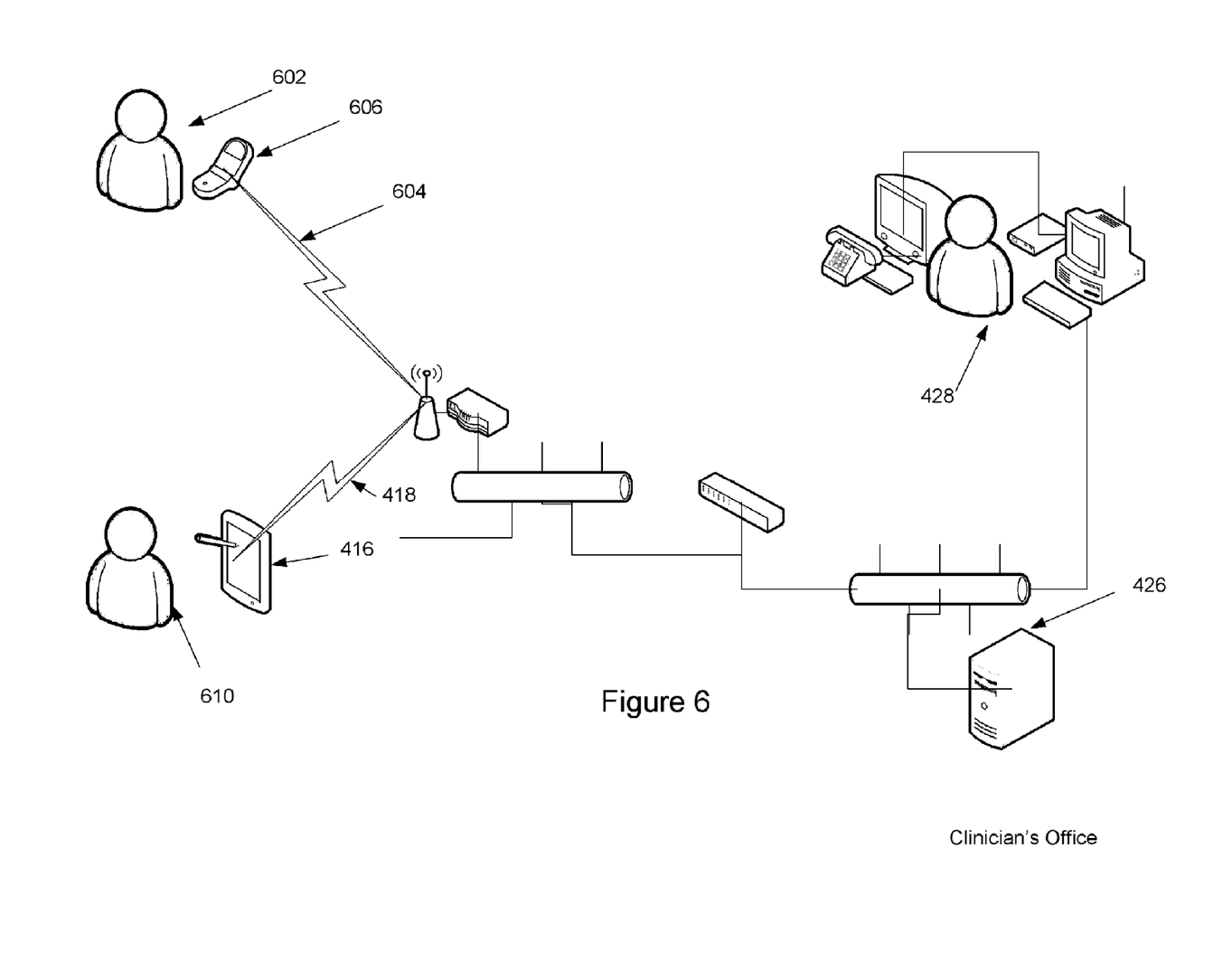
FIG. 6 illustrates a system diagram of various exemplary users interfacing with the system, a clinician's office computer equipment and a person in the clinician's office, according to an illustrative embodiment of the invention.

As seen in FIG. 6, in one embodiment, a user 610 uses his handset to activate the PSEAT. The test activation may have been triggered by the user 610, by an automated utility within a calendar (either located within the handset 416 memory or that of a server 426 within the network), by a third interested party (such as clinician 428 or concerned family member). The user 610 proceeds to take the test and the results are communicated via the wireless network 418 to the clinician's server 426.

In one embodiment, a user 602 takes the test, which is communicated via a bandwidth limited link 604, such as SMS texting. SMS messages are limited to message packets of length no larger than 160 characters. In such an embodiment, the handset 606 software would capture the user input as a set of Cartesian coordinates or vectors replicating the user's input 110, and these would be transmitted via the cellular network and Internet to the clinician's office server 426. The software there would receive the one or more messages containing the user data and ID. The receiving server 426 would then replicate the series of vectors in order to re-construct the test taken by the user.

Regardless of the method or link used to communicate the test results, in one embodiment, a clinician 428, may be used to check the test results, and if they are found wanting, send a request to the user 610 for a re-test. This last function may be performed automatically at either the handset 416 level, or at the receiving server 426 level, or it may be as simple as placing/sending a phone call or text message to the patient or their caretaker. One of the ways to do that would be to ensure that a continuity analysis is done on the test data points. If the data points do not form a satisfactory area (be it a complete circle, or other commonly known Amsler test protocols), the user 610 would be notified to perform a re-test.

The ability to save multiple images over time aids the Doctor in evaluating disease progression. In one embodiment, the device itself can be programmed to remind the user of the need to perform the test at a specific time. In one embodiment, the test may be commanded remotely by either a treating clinician or other $3^{rd}$ parties over cellular, 3G, WiFi, WiMax, Internet or other such links.

In one embodiment, the implementation of such a test in such a portable electronic device would be enhanced by the ability of such a device to be either continually or partially connected to the treating clinician's facility. The data captured would be uploaded immediately or with minimal delay, allowing for quick evaluation (and even instructions) by a live technician, and or even a quick remote evaluation by a qualified clinician 428 as well as a re-test if necessary.

In order to assist the clinicians in their analysis, the stored test results (whether they are the images or the coordinates generated by the patient interaction) may be subjected to mathematic or statistical manipulation via the analysis of one or more of the tests. In one mode, one or more tests may be subjected to comparison, covariance, statistical deviation, Kalman filtering or other manipulation suitable to discern a trend in the patient condition over time.

In one embodiment, the device would be included as part of an Electronic Medical Record (EMR) system where the test is performed by a clinician and the recorded Amsler image is saved in the patient's electronic medical record for later review.

EXAMPLE

The function and advantages of these and other embodiments of the invention can be further understood from the examples below, which illustrate the benefits and/or advantages of the one or more systems and techniques of the invention but do not exemplify the full scope of the invention.

Figure 7A:
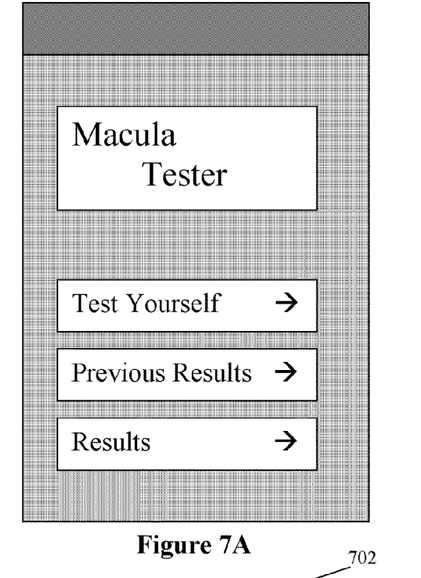
FIGS. 7A-7F illustrate a series of exemplary application screens, according to an illustrative embodiment of the invention.

This example describes the performance of a test by a patient in accordance with one or more embodiments of the invention. To begin with, the user proceeds to power up the application within the hand-held device. In one embodiment this is an Apple iPhone or iTouch device, capable of driving the graphical representation of the Amsler Chart in its display. As seen in FIG. 7A the menu displays three options, including A) Test Yourself, B) Previous Results (review) and C) Settings.

Figure 7B:
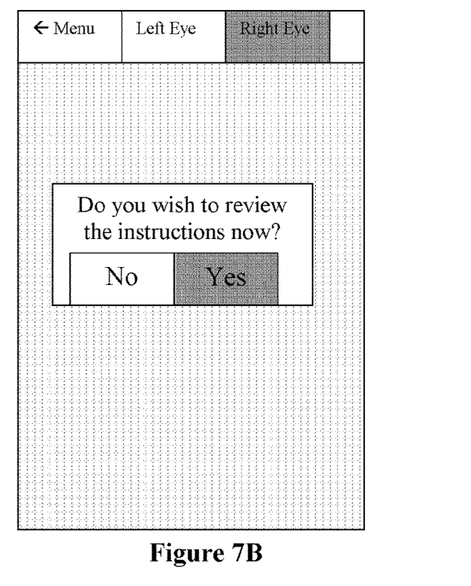
Figure 7C:
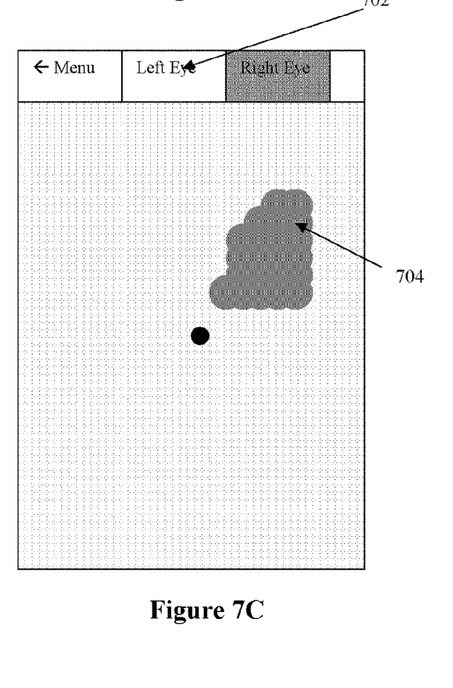
Figure 7D:
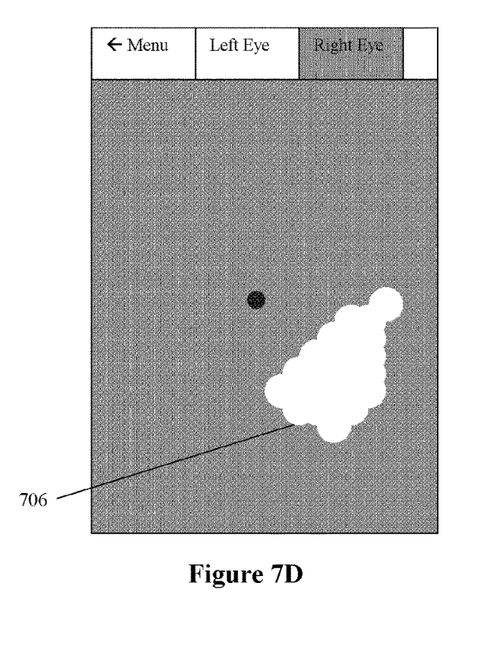

To perform the test, the user selects A) Test Yourself. As seen in FIG. 7B, the unit proceeds to ask the user if they would like to review the instructions. Let's assume the user knows, at which point the next step is to whether the test if for the left eye or the right eye. In this example, the user selects to test the left eye 702 on FIG. 7C, and by pointing at the portion of the screen perceived defectively by the left eye, the user selects the area 704. Note that the user may have instead selected to test the right eye using a blue background FIG. 7D, and selected a different area 706.

Figure 7E:
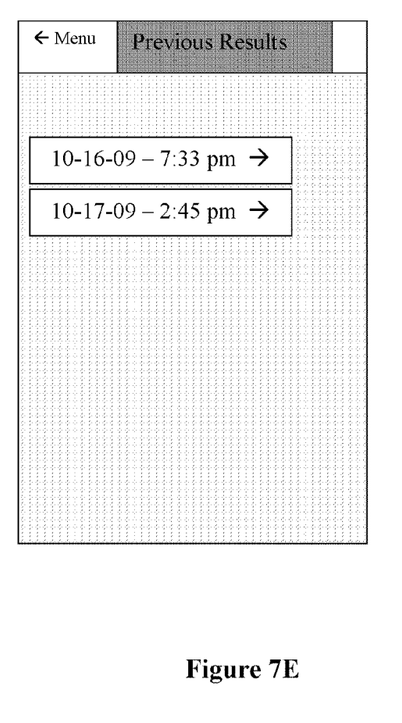
Figure 7F:
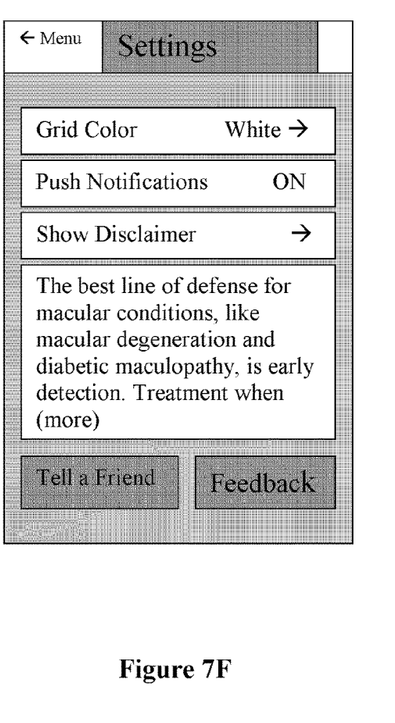

Having self-administered the test, the user then stores the results FIG. 7E for uploading to the clinician under one of the methods described above. Besides being able to review previous results, the user may also be able to adjust the settings FIG. 7F. Note that in addition, the clinician may be able to alter these settings remotely as described above. In this example, the user selects (from FIG. 7A) the latter, C) Settings. In one embodiment, the choices include selecting the Grid Color (preferably white, black or blue), whose choice is limited only by the colors possible by the portable computer display. In one embodiment, the user is given the choice of "Push Notification", which allows for notification to the care provider or patients support group. This push is accomplished by any of the links of which the portable computing device is capable, as described before (e.g. cell network, 3G, base station Internet connection, movable internet connection, etc.). In addition, the test settings may include notifications to friends of the application, as well as feedback to developers of any features.

CONCLUSION

In concluding the detailed description, it should be noted that it would be obvious to those skilled in the art that many variations and modifications can be made to the preferred embodiment without substantially departing from the principles of the present invention. Also, such variations and modifications are intended to be included herein within the scope of the present invention as set forth in the appended claims. Further, in the claims hereafter, the structures, materials, acts and equivalents of all means or step-plus function elements are intended to include any structure, materials or acts for performing their cited functions.

It should be emphasized that the above-described embodiments of the present invention, particularly any preferred embodiments are merely possible examples of the implementations, merely set forth for a clear understanding of the principles of the invention. Any variations and modifications may be made to the above-described embodiments of the invention without departing substantially from the spirit of the principles of the invention. All such modifications and variations are intended to be included herein within the scope of the disclosure and present invention and protected by the following claims.

The present invention has been described in sufficient detail with a certain degree of particularity. The utilities thereof are appreciated by those skilled in the art. The invention may be embodied in other specific forms without departing from the spirit or essential characteristics thereof. The forgoing embodiments are therefore to be considered in all respects illustrative, rather than limiting of the invention. It is understood to those skilled in the art that the present disclosure of embodiments has been made by way of examples only and that numerous changes in the arrangement and combination of parts may be resorted without departing from the spirit and scope of the invention as claimed. Accordingly, the scope of the present invention is defined by the appended claims rather than the forgoing description of embodiments.

What is claimed is:

1. A portable electronic device comprising;
   a display capable of displaying an electronic representation of an Amsler chart;
   a user interface adapted to receive user inputs that capture the portion of said display selected by the user;
   a processor and memory device for storing said user inputs data, as well as ancillary user information, and test results;
   a touch sensitive display;
   a connection for uploading test results to a another computer; and
   said connection is wireless.

2. The portable electronic device of claim 1 wherein;
   said wireless network is a Wi-Fi network.

3. The portable electronic device of claim 1 wherein;
   said wireless network is a cell phone network.

4. The portable electronic device of claim 1 wherein;
   said wireless network is a 3G or WiMax network.

5. A portable electronic device comprising;
   a display capable of displaying an electronic representation of an Amsler chart;
   a user interface adapted to receive user inputs that capture the portion of said display selected by the user;
   a processor and memory device for storing said user inputs data, as well as ancillary user information, and test results;
   a connection for uploading test results to a another computer;
   said connection is wireless.

6. The portable electronic device of claim 5 wherein;
   said wireless network is a Wi-Fi network.

7. The portable electronic device of claim 5 wherein;
   said wireless network is a cell phone network.

8. The portable electronic device of claim 5 wherein;
   said wireless network is a 3G or WiMax network.

9. Computer readable medium for storing computer code for using a portable electronic device, the computer readable medium comprising;
   computer code for causing the display of said portable electronic device to display an electronic representation of an Amsler chart;
   computer code for causing portable electronic device to execute a set of instructions, which when executed by said portable electronic device will allow it to capture and store the portions of said display selected by the user;
   computer code for storing in memory, in addition to the selected portions of the screen, the user identity and ancillary information;
   computer code for using a portable electronic device with a touch screen; and
   computer code for causing the portable electronic device to execute another set of instructions, which when executed by said portable electronic device cause said device to upload the stored test results to another computer via a wireless computer network.

10. The computer readable medium as recited in claim 9, wherein;
    said wireless network is a Wi-Fi network.

11. The computer readable medium as recited in claim 9, wherein;
    said wireless network is a cell phone network.

12. The computer readable medium as recited in claim 9, wherein;
    said wireless network is a 3G or WiMax wireless network.

\* \* \* \* \*